United States Patent [19]

Homeyer

[11] Patent Number: 5,129,258
[45] Date of Patent: Jul. 14, 1992

[54] METHOD FOR DETERMINING TEMPERATURE WITH THE AID OF THE INTERNAL RESISTANCE OF A LAMBDA SENSOR

[75] Inventor: Manfred Homeyer, Markgröningen, Fed. Rep. of Germany

[73] Assignee: Robert Bosch GmbH, Stuttgart, Fed. Rep. of Germany

[21] Appl. No.: 477,923
[22] PCT Filed: Oct. 6, 1989
[86] PCT No.: PCT/DE89/00637
§ 371 Date: Jun. 21, 1990
§ 102(e) Date: Jun. 21, 1990
[87] PCT Pub. No.: WO90/04764
PCT Pub. Date: May 3, 1990

[30] Foreign Application Priority Data

Oct. 21, 1988 [DE] Fed. Rep. of Germany ....... 3835852

[51] Int. Cl.$^5$ .............................. G01M 15/00
[52] U.S. Cl. ..................................... 73/116
[58] Field of Search .............. 204/153.18, 408, 425; 73/116; 374/144

[56] References Cited

U.S. PATENT DOCUMENTS 4,376,026 3/1983 Hoffman et al. ............ 204/408 X
4,419,190 12/1983 Dietz et al. .................... 204/408
4,742,808 5/1988 Blümel et al. ..................... 123/489

Primary Examiner—Jerry W. Myracle
Attorney, Agent, or Firm—Walter Ottesen

[57] ABSTRACT

In a method for determining the exhaust gas temperature, the internal resistance of a lambda sensor is measured, and it is determined whether lean or rich mixture is present. Depending on which mixture type is present, the exhaust gas temperature associated with the measured internal resistance value is read out from one of two internal resistance value/exhaust gas temperature characteristic curves. This method can be used correspondingly for determining the sensor temperature from the internal resistance.

The exhaust gas temperature determined as above only applies accurately for steady-state cases. In order to obtain satisfactory values even in non-steady-state cases, the exhaust gas temperature is averaged in a sliding manner. The present exhaust gas temperature is determined from the particular average value and the particular rise in the exhaust gas temperature/time curve.

The mentioned methods permit the exhaust gas temperature to be determined without a separate temperature measuring element. With a single measurement, namely that of the internal resistance, the sensor temperature and the exhaust gas temperature can be determined with a high degree of accuracy.

7 Claims, 1 Drawing Sheet

METHOD FOR DETERMINING TEMPERATURE WITH THE AID OF THE INTERNAL RESISTANCE OF A LAMBDA SENSOR

FIELD OF THE INVENTION

The invention relates to a method for determining the temperature of a lambda sensor and/or the temperature of the exhaust gas surrounding it. The invention also relates to an apparatus for determining the exhaust gas temperature.

BACKGROUND OF THE INVENTION

It is known that the internal resistance of a lambda sensor drops significantly with increasing temperature. There is a definite relationship between the sensor temperature and the internal resistance. This relationship is used to determine the sensor temperature from a measurement of the internal resistance, as described, for example, in U.S. Pat. No. 4,419,190.

The temperature of the lambda sensor is determined in the case of an unheated sensor exclusively and in the case of a heated sensor predominantly by the temperature of the exhaust gas surrounding it. This temperature is determined according to the state of the art with the aid of a separate measuring sensor.

It is the object of the invention to specify methods for determining the temperatures of a lambda sensor and/or of the exhaust gas surrounding it with the methods being simple but nevertheless operating precisely. Furthermore, the invention is based on the object of specifying an apparatus of simple configuration for determining the exhaust gas temperature.

SUMMARY OF THE INVENTION

The method of the invention is for determining the temperature of the exhaust gas of an internal combustion engine and includes the steps of: measuring the internal resistance of a lambda sensor arranged in the exhaust gas; and, determining the exhaust gas temperature with the aid of a known relationship between internal resistance and exhaust gas temperature for the steady-state case.

The sensor temperature is determined with the aid of a known relationship between internal resistance and sensor temperature. The temperature of the lambda sensor is determined by detecting the lambda value; and, in the case of a rich mixture, a relationship between internal resistance and sensor temperature is used which was determined for a rich mixture, and in the case of a lean mixture, a relationship between internal resistance and sensor temperature is used which was determined for a lean mixture.

Both methods are distinguished by the fact that they perform a temperature determination with the aid of the internal resistance of a lambda sensor arranged in the exhaust gas. The method according to the invention for determining the exhaust gas temperature is based on the recognition that not only is the relationship between internal resistance and sensor temperature definite, but also that, provided there are steady-state conditions, the relationship between sensor temperature and exhaust gas temperature is definite for a particular present arrangement. Accordingly, there is, for the steady-state case, a definite relationship between internal resistance and exhaust gas temperature. This makes it possible initially to measure the relationship between exhaust gas temperature and internal resistance and then to determine, with the aid of this known relationship, the exhaust gas temperature for the steady-state case from the internal resistance measured in the normal manner. In this connection, it is irrelevant whether the sensor is heated or unheated. Resulting differences in the relationship between internal resistance and exhaust gas temperature are automatically taken into account if the relationship between internal resistance and exhaust gas temperature is measured.

In order to be able to determine the exhaust gas temperature from the internal resistance even in the non-steady-state case, the temperature obtained from the steady-state relationship is corrected with the aid of increase of the time/temperature curve at the particular instant.

It is also advantageous to perform a correction which allows for the fact that different relationships between internal resistance and exhaust gas temperature exist for leaner and richer mixtures, to the effect that with a particular identical exhaust gas temperature, in rich mixtures, a higher internal resistance is measured than in lean mixtures.

Another embodiment of the method according to the invention is distinguished by the fact that it utilizes the relationships just described in conjunction with the determination of the exhaust gas temperature for determining the sensor temperature. The same sensor temperature value is no longer determined in each case, as previously, for each internal resistance value for lean and rich mixture, but rather a higher value is determined for lean mixture than for rich mixture. This occurs in a particularly advantageous manner in that the relationship between internal resistance and sensor temperature is determined for a mixture type, for example for lean mixture, and this relationship is used directly if the mixture type for which the determination occurred is present, while a correction is performed if the other mixture type is present.

The apparatus according to the invention for determining the exhaust gas temperature has a means for measuring the internal resistance of a lambda sensor and a means for determining the exhaust gas temperature from the internal resistance.

BRIEF DESCRIPTION OF THE DRAWING

The invention is described in greater detail below with reference to embodiments illustrated by figures, in which.

DESCRIPTION OF THE PREFERRED EMBODIMENTS OF THE INVENTION

Figure 1:
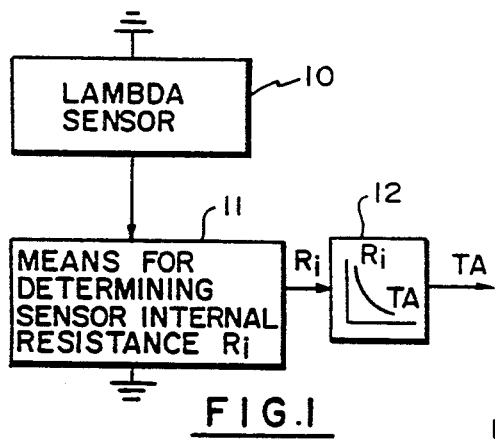
FIG. 1 shows a block circuit diagram of an apparatus for determining the exhaust gas temperature with the aid of the internal resistance of a lambda sensor arranged in the exhaust gas.

In the arrangement according to FIG. 1, a lambda sensor 10 located in the exhaust gas of an internal combustion engine is connected to a means 11 for determining the sensor internal resistance $R_i$. This means determines the internal resistance, for example according to the above-mentioned method explained in U.S. Pat. No. 4,419,190 or according to a method as described in U.S. Pat. No. 4,742,808. A characteristic curve memory 12 is addressed with the internal resistance value determined for the particular instant, and, as a result, the exhaust gas temperature TA associated with the determined internal resistance value is read out. The characteristic curve was previously determined in that steady-state exhaust gas temperatures were set, the latter were measured with the aid of a separate temperature sensor and the associated internal resistance value of the sensor was determined for each exhaust gas temperature. The associated exhaust gas temperature for each internal resistance value was stored in the characteristic curve memory 12.

Figure 2A:
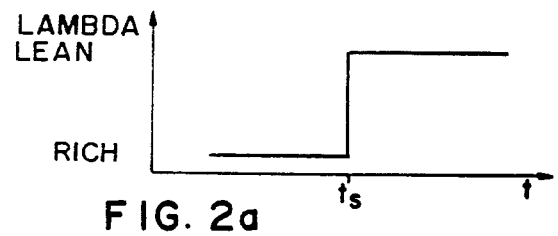
FIGS. 2a and 2b show diagrams for explaining the dependence of the sensor internal resistance (2b) on the lambda value (2a)
Figure 2B:
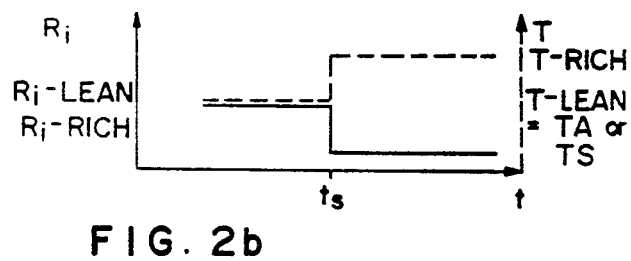

With reference to FIG. 2, a fine detail will now be explained which is to be noted when determining the relationship between internal resistance value and temperature. It is assumed that the exhaust gas temperature and therefore also the sensor temperature is kept constant over the time t. However, assuming that the sensor is located up to a time $t_S$ in the exhaust gas which originates from the combustion of a rich mixture, and thereafter in the exhaust gas that originates from the combustion of a lean mixture. The lambda value thus increases rapidly at the time $t_S$ from rich to lean. From FIG. 2b it can be seen that the internal resistance falls rapidly with the rapid increase of the lambda value. It should therefore be ensured that the relationship between internal resistance and exhaust gas temperature TA or sensor temperature TS for determining a characteristic curve is always determined for the same mixture type. If the characteristic curve was recorded with a lean mixture, there results for the internal resistance value $R_i$-lean, represented on the left in FIG. 2b, the correct exhaust gas or sensor temperature value as indicated in FIG. 2b by the right-hand scale. However, for a rich mixture, an excessively high temperature value T-rich results from the characteristic curve recorded for lean mixture.

There are several possible ways of taking account of the lambda dependency in the relationship between internal resistance and exhaust gas temperature or sensor temperature. All require the lambda value to be measured. The first possibility is that in each case different internal resistance value/temperature characteristic curves are used for rich mixtures and for lean mixtures. Depending on the lambda value, the associated characteristic curve is then selected, and, from the characteristic curve, the exhaust gas temperature or sensor temperature is read out with the aid of the internal resistance value present. The next possibility consists in using only a single characteristic curve, for example one which was recorded for lean mixtures, and correcting this characteristic curve for the other mixture type, in the example for rich mixtures. If, in the example, a lean mixture is present, the temperature value read out from the characteristic curve is used directly, while if a rich mixture is present, a difference value is subtracted which, in the example, is a temperature difference value. It has been shown that the difference value is approximately ½% of the absolute exhaust gas temperature, that is approximately 5° C. at an exhaust gas temperature of approximately 750° C. The difference value required for correction, however, does not change exactly proportionally to the absolute temperature of the exhaust gas or of the sensor. Therefore, a constant difference value can also be used with a high degree of accuracy, for example 5.5° C. in the sensors used in tests. It was found that there are also small dependencies on the magnitude of the lambda value. All the mentioned dependencies are, however, so small that under all conditions a fixed correction value was sufficient in the sensors used in the test to obtain satisfactory results. If extremely accurate results are required, characteristic fields must be used in which a multiplicity of internal resistance value/temperature characteristic curves is stored for each of the different lambda values.

Instead of initially converting an internal resistance value into a temperature and then performing corrections, it is also possible to first correct the internal resistance and then to convert the internal resistance to a temperature. Thus, for example when a lean mixture is present, each internal resistance value determined is taken over in unchanged form, in contrast a difference value is added to each internal resistance value determined with rich mixture. With the internal resistance value corrected in this way, the associated temperature is then read out of an internal resistance value/temperature characteristic curve determined for lean mixtures.

A preferred method sequence which takes into account the points described above will now be described with reference to FIG. 3. In a step s1, the present internal resistance for $R_i$ is determined according to a known method. In a step s2, the exhaust gas temperature TA is determined from a first characteristic curve and the sensor temperature TS from a second characteristic curve, each in dependence on the determined internal resistance value. In a step s3, the actual lambda value is measured. If it becomes apparent in a step s4 that a lean mixture is present, a subprogram follows immediately as step s5, in which the values for exhaust gas temperature and sensor temperature are used. The method then returns to step s1. If, in contrast, it becomes clear in step s4 that a lean mixture is not present but rather a rich one, the exhaust gas temperature value TA is corrected in a step s6 in that a fixed differential value ΔT is subtracted from the value determined in step s2. The same difference is subtracted from the sensor temperature TS as was likewise calculated in step s2. The temperatures corrected in this way are then used in the subprogram according to step s5.

It is to be noted that the exhaust gas temperature TA and the sensor temperature TS do not have to be both determined together. The described correction method for allowing for the mixture type can also be used individually for any temperature. However, it is of particular advantage to perform the method for both temperatures. Two temperatures can then be determined with a high degree of accuracy, at any rate for steady-state cases, with a single measurement, namely that of the internal resistance. There are numerous possibilities for the type of correction, as explained further above.

Figure 3:
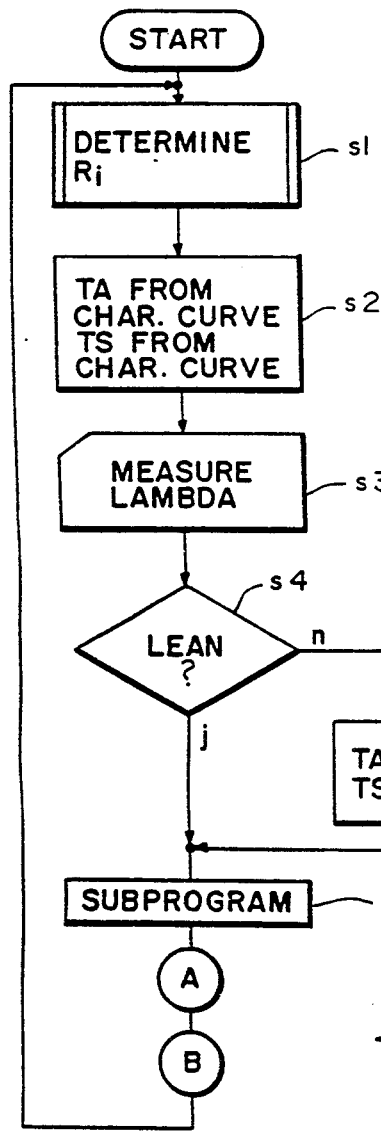
FIG. 3 shows a flow diagram for explaining how sensor temperature and exhaust gas temperature are determined with the aid of the internal resistance of a sensor and are corrected taking into account the mixture type present; and, FIG. 4 shows a flow diagram of a sub-method for determining the exhaust gas temperature in the steady-state case.

In the method sequence according to FIG. 3, two marks A and B are entered after the step s5 before the return to step s1. Between these marks, a sub-method can be run through which permits an extremely accurate determination of the exhaust gas temperature even in non-steady-state cases. This method will now be explained with reference to FIG. 4.

Figure 4:
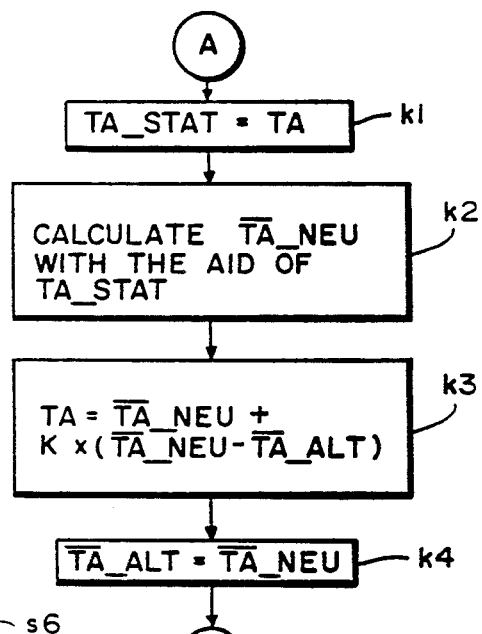

According to FIG. 4, a step k1 follows the mark A, this step serving only a formal purpose; namely, the exhaust gas temperature value TA is merely provided with the name TA_STAT. This indicates that this is the exhaust gas temperature which was determined for the present time from a relationship between internal resistance value and exhaust gas temperature, this relationship applying for steady-state conditions. In a step k2, an average value $\overline{TA\_NEU}$ is determined with the aid of the most recent value of TA_STAT. For example, averaging occurs in a sliding manner over the respective last four values. Or, the last average value is used weighted with three quarters, and, to this value, the new value is added weighted with one quarter. How much data is used for averaging and how the averaging is performed depends on the respective application.

Before the step k3 which now follows is explained in greater detail, more details will be given on the step k4 which follows thereafter. According to step k4, the new average value $\overline{TA\_NEU}$ calculated in step k2 is termed the old average value $\overline{TA\_ALT}$. In step k3, the new average value $\overline{TA\_NEU}$ calculated in step k2 is thus available, as well as the average value calculated in the previous passage in step k2 and which now bears the name $\overline{TA\_ALT}$. In step k3, with the aid of these values and of the value TA_STAT, the exhaust gas temperature is calculated according to step k1 as follows:

$$TA = \overline{TA\_NEU} + K \times (\overline{TA\_NEU} - \overline{TA\_ALT})$$

K is a constant which in tests is determined in such a way that, from the mentioned equation, a value is obtained for the exhaust gas temperature even in non-steady-state cases which coincides as accurately as possible with the respective value as was acquired by means of a separate temperature measuring means. If the constant K is determined by measurements for a predetermined arrangement, it supplies satisfactory results for almost all non-steady-state cases.

I claim:

1. A method for determining the temperature of the exhaust gas of an internal combustion engine, the method comprising the steps of:
   measuring the internal resistance of a lambda sensor arranged in the exhaust gas;
   determining the exhaust gas temperature with the aid of a known relationship between internal resistance and exhaust gas temperature for the steady-state case;
   determining the rise in the exhaust gas temperature-time curve in each case at the pertinent time; and,
   adding the rise value multiplied by a constant to the temperature, the constant being predetermined in tests in such a way that, with the previously mentioned method steps, as accurate a matching as possible to the actual exhaust gas temperature occurs.

2. A method for determining the temperature of the exhaust gas of an internal combustion engine, the method comprising the steps of:
   measuring the internal resistance of a lambda sensor arranged in the exhaust gas; and,
   determining the exhaust gas temperature with the aid of a known relationship between internal resistance and an averaged temperature of the exhaust gas.

3. A method for determining the lambda value of the exhaust gas of an internal combustion engine, the method comprising the steps of:
   measuring the internal resistance of a lambda sensor arranged in the exhaust gas;
   determining the exhaust gas temperature with the aid of a known relationship between internal resistance and exhaust gas temperature for the steady-state case; and,
   in the case of a rich mixture, using a relationship between internal resistance and exhaust gas temperature which was determined for a rich mixture, and in the case of a lean mixture, using a relationship between internal resistance and exhaust gas temperature which was determined for a lean mixture.

4. The method of claim 3, wherein a relationship between internal resistance and exhaust gas temperature is used which was determined for a first mixture type, and when the lambda value indicates the first mixture type, the conversion of internal resistance value into exhaust gas temperature occurs in a conversion step according to the relationship determined, but, if the lambda value indicates the other mixture type, in addition to the mentioned conversion step, a further conversion step occurs, according to which a temperature difference value is subtracted if the first mixture type is a lean mixture, but in contrast, is added if the first mixture type is a rich mixture.

5. A method for determining the temperature of the exhaust gas of an internal combustion engine, the method comprising the steps of:
   measuring the internal resistance of a lambda sensor arranged in the exhaust gas;
   determining the exhaust gas temperature with the aid of a known relationship between internal resistance and exhaust gas temperature for the steady-state case; and,
   determining the sensor temperature with the aid of a known relationship between internal resistance and sensor temperature.

6. The method for determining the temperature of a lambda sensor, according to claim 5, wherein the lambda value is detected, and in the case of a rich mixture, a relationship between internal resistance and sensor temperature is used which was determined for a rich mixture, and in the case of a lean mixture, a relationship between internal resistance and sensor temperature is used which was determined for a lean mixture.

7. A method for determining the temperature of the exhaust gas of an internal combustion engine, the method comprising the steps of:
   (a) measuring the internal resistance of a lambda sensor arranged in the exhaust gas;
   (b) determining a value of the exhaust gas temperature TA from a first characteristic curve and a value of the sensor temperature TS from a second characteristic curve;
   (c) measuring the actual lambda value to ascertain the condition of the mixture actually present and, if said mixture is a lean mixture, then
   (d) utilizing said exhaust gas temperature TA and said sensor temperature TS and return to the step (a); however, if a rich mixture is present, then,
   (e) correcting said exhaust gas temperature TA by subtracting a fixed differential value $\Delta T$ from said value of said exhaust gas temperature determined in step (b) and correcting said sensor temperature TS by also subtracting said fixed differential value $\Delta T$ from said value of said sensor temperature determined in step (b) and then return to step (a).

* * * * *